US011576600B2

(12) United States Patent
Lee et al.

(10) Patent No.: US 11,576,600 B2
(45) Date of Patent: Feb. 14, 2023

(54) MODULAR ELECTRONIC DEVICE FOR MEASURING BIO-SIGNALS

(71) Applicant: Samsung Electronics Co., Ltd., Suwon-si (KR)

(72) Inventors: Jinchoul Lee, Suwon-si (KR); Minhyuk Nam, Suwon-si (KR); Yunguk Lee, Suwon-si (KR); Hyoungil Song, Suwon-si (KR); Chunsik Choi, Suwon-si (KR); Seungnyun Kim, Suwon-si (KR); Yongsang Yun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 142 days.

(21) Appl. No.: 17/011,820

(22) Filed: Sep. 3, 2020

(65) Prior Publication Data

US 2021/0059553 A1  Mar. 4, 2021

(30) Foreign Application Priority Data

Sep. 3, 2019 (KR) .......................... 10-2019-0108649

(51) Int. Cl.
*A61B 5/257* (2021.01)
*A61B 5/259* (2021.01)
(Continued)

(52) U.S. Cl.
CPC .............. *A61B 5/259* (2021.01); *A61B 5/333* (2021.01); *A61B 5/339* (2021.01)

(58) Field of Classification Search
None
See application file for complete search history.

(56) References Cited

U.S. PATENT DOCUMENTS 4,270,543 A * 6/1981 Tabuchi ................... A61B 5/25
600/391
8,170,683 B2  5/2012 Wahlgren et al.
(Continued)

FOREIGN PATENT DOCUMENTS

CN       107669261 A    2/2018
JP       2009518153 A   5/2009
(Continued)

OTHER PUBLICATIONS

International Search Report and Written Opinion of the International Searching Authority in connection with International Application No. PCT/KR2020/011760 dated Dec. 11, 2020, 12 pages.

*Primary Examiner* — Kennedy Schaetzle

(57) ABSTRACT

The electronic device includes a pad module and a main module. At least part of the patch module is attached to a user to obtain a bio-signal of the user. The pad module includes a first housing and a plurality of first electrodes disposed in the first housing. The main module is configured to record the bio-signal of the user that is transferred through the pad module. The main module includes a second housing that is coupled with the first housing in a first direction. The main module also includes a plurality of second electrodes disposed in the second housing. The plurality of second electrodes are configured to make electrical contact with the plurality of first electrodes. The main module further includes a plurality of magnetic bodies disposed in the second housing to correspond to positions of the plurality of second electrodes.

20 Claims, 9 Drawing Sheets

(51) Int. Cl.
*A61B 5/333* (2021.01)
*A61B 5/339* (2021.01)

(56) References Cited

U.S. PATENT DOCUMENTS

| | | | |
|---|---|---|---|
| 8,626,261 B2 | 1/2014 | Ko et al. | |
| 9,211,400 B2 | 12/2015 | Bachinski et al. | |
| 9,325,107 B2 | 4/2016 | Karls et al. | |
| 9,662,440 B2 | 5/2017 | Yodfat et al. | |
| 9,901,273 B2 | 2/2018 | Ichida et al. | |
| 2008/0215035 A1 | 9/2008 | Yodfat et al. | |
| 2008/0312524 A1 | 12/2008 | Solosko et al. | |
| 2009/0105574 A1* | 4/2009 | Young | A61B 5/332 600/509 |
| 2009/0157149 A1 | 6/2009 | Wahlgren et al. | |
| 2013/0023816 A1 | 1/2013 | Bachinski et al. | |
| 2014/0213880 A1* | 7/2014 | Banet | A61B 5/0535 600/393 |
| 2015/0111399 A1 | 4/2015 | Karls et al. | |
| 2015/0173639 A1 | 6/2015 | Ichida et al. | |
| 2015/0201858 A1* | 7/2015 | Ganim | A61B 5/30 600/393 |
| 2015/0374255 A1* | 12/2015 | Vasapollo | A61B 5/6814 600/383 |
| 2017/0181698 A1* | 6/2017 | Wiedenhoefer | A61B 1/041 |
| 2017/0224912 A1 | 8/2017 | Yodfat et al. | |
| 2018/0078163 A1* | 3/2018 | Welch | A61B 5/332 |
| 2019/0239769 A1 | 8/2019 | Lee et al. | |
| 2020/0029825 A1* | 1/2020 | Tang | A61B 5/0205 |

FOREIGN PATENT DOCUMENTS

| | | |
|---|---|---|
| JP | 2011505981 A | 3/2011 |
| KR | 10-2012-0016474 A | 2/2012 |
| KR | 10-2016-0143381 A | 12/2016 |
| KR | 10-2018-0126949 A | 11/2018 |

* cited by examiner

MODULAR ELECTRONIC DEVICE FOR MEASURING BIO-SIGNALS

CROSS-REFERENCE TO RELATED APPLICATION

This application is based on and claims priority under 35 U.S.C. § 119 to Korean Patent Application No. 10-2019-0108649, filed on Sep. 3, 2019, in the Korean Intellectual Property Office, the disclosure of which is incorporated by reference herein its entirety.

BACKGROUND

1. Field

The disclosure relates to an electronic device for measuring bio-signals, the electronic device being attached to a user's body.

2. Description of Related Art

An electronic device (e.g., an electrocardiograph device) for measuring bio-signals (e.g., an electrocardiogram) may be used in various ways depending on the types of tests (e.g., a 12 lead ECG test, an exercise ECG test, and an ambulatory ECG test). According to an embodiment, the electronic device for measuring bio-signals may include an electrode pad and a Holter monitor to measure an ambulatory ECG.

The above information is presented as background information only to assist with an understanding of the disclosure. No determination has been made, and no assertion is made, as to whether any of the above might be applicable as prior art with regard to the disclosure.

SUMMARY

An electronic device for measuring bio-signals may include an electrode pad and a Holter monitor. The electrode pad may be attached to at least part of a user's body, and the Holter monitor may be connected with the electrode pad through a connecting wire. In an operating environment of the electronic device for measuring bio-signals, the user has to carry the electrode pad and the Holter monitor, which is connected with the electrode pad, for a set period of time. Therefore, foreign matter or moisture may infiltrate into the electrode pad and the Holter monitor during the user's daily life. In this case, the electronic device for measuring bio-signals may malfunction, or may collect incorrect data.

Furthermore, when the user removes and re-attaches the electrode pad according to necessity or situation (e.g., shower), attachment performance of the electrode pad may be degraded. In this case, the electrode pad may be incorrectly attached to the user's body, and therefore the electronic device for measuring bio-signals cannot normally collect data.

Aspects of the disclosure are to address at least the above-mentioned problems and/or disadvantages and to provide at least the advantages described below. Accordingly, an aspect of the disclosure is to provide an electronic device for measuring bio-signals.

In accordance with an aspect of the disclosure, an electronic device for supporting measurement of a bio-signal includes a pad module, at least part of which is attached to a user's body to obtain a bio-signal of the user and a main module that records the user's bio-signal transferred through the pad module. The pad module includes a plurality of first electrodes and a first housing in which the plurality of first electrodes are disposed. The main module includes a plurality of second electrodes that make electrical contact with the plurality of first electrodes, a second housing in which the plurality of second electrodes are disposed, the second housing being coupled with the first housing in a first direction, and a plurality of magnetic bodies disposed in the second housing to correspond to positions of the plurality of second electrodes, in which the plurality of magnetic bodies allow the plurality of first electrodes and the plurality of second electrodes to be brought into contact with each other by a magnetic force. When the plurality of first electrodes and the plurality of second electrodes are brought into contact with each other by an attraction force of the magnetic bodies, the second housing is coupled with the first housing such that a periphery of the second housing is engaged with a periphery of the first housing.

In accordance with another aspect of the disclosure, an electronic device for supporting measurement of a bio-signal includes a pad module, at least part of which is attached to a user's body to obtain a bio-signal of the user and a main module that records the user's bio-signal transferred through the pad module. The pad module includes a plurality of first electrodes, a first housing in which the plurality of first electrodes are disposed, and a packing member disposed on a periphery of the inside of a first sidewall included in the first housing. The main module includes a plurality of second electrodes that make electrical contact with the plurality of first electrodes, a second housing in which the plurality of second electrodes are disposed, the second housing being coupled with the first housing in a first direction, and a plurality of magnetic bodies disposed in the second housing to correspond to positions of the plurality of second electrodes, in which the plurality of magnetic bodies allow the plurality of first electrodes and the plurality of second electrodes to be brought into contact with each other by a magnetic force. The second housing includes a protrusion disposed in a gap between the packing member and the first sidewall when the plurality of first electrodes and the plurality of second electrodes are brought into contact with each other by an attraction force of the magnetic bodies.

Other aspects, advantages, and salient features of the disclosure will become apparent to those skilled in the art from the following detailed description, which, taken in conjunction with the annexed drawings, discloses various embodiments of the disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Hereinafter, various embodiments of the disclosure will be described with reference to the accompanying drawings. However, those of ordinary skill in the art will recognize that modifications, equivalents, and/or alternatives on the various embodiments described herein can be variously made without departing from the scope and spirit of the disclosure.

Figure 1:
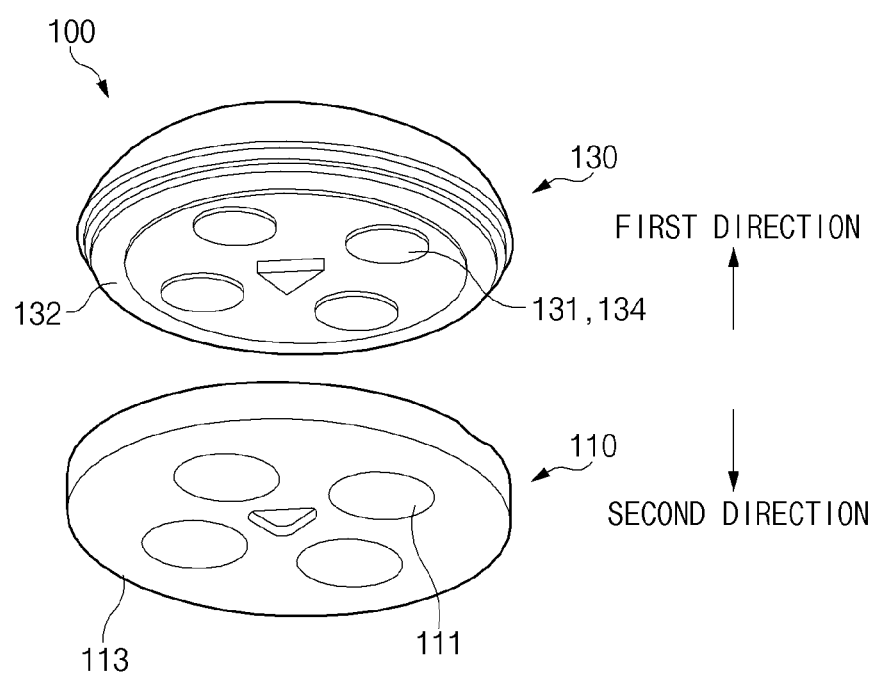
FIG. 1 illustrates a view of a rear side of an electronic device according to an embodiment.

FIG. 1 illustrates a view of a rear side of an electronic device for measuring bio-signals according to an embodiment.

Referring to FIG. 1, the electronic device 100 for measuring bio-signals according to an embodiment may include a pad module 110 and a main module 130 that are separated from, or combined with, each other. In the following description, "modules" may include hardware modules implemented by a combination of electronic or mechanical components.

According to an embodiment, one surface of the pad module 110 may be brought into contact with a user's body, and an opposite surface of the pad module 110 may be coupled to the main module 130. For example, a plurality of first electrodes 111 of the pad module 110 may be disposed to be exposed to the outside through one surface of a first housing 113.

According to an embodiment, the first electrodes 111 may be brought into direct contact with the user's body, or may be brought into indirect contact with the user's body through a medium (e.g., another electrode electrically connectable with the first electrodes 111). For example, at least parts of the first electrodes 111 may be exposed through one surface and an opposite surface of the first housing 113. According to various embodiments, the first electrodes 111 may obtain bio-signals (e.g., action currents) of the user.

According to an embodiment, the first housing 113 may form a first arrangement space in which the plurality of first electrodes 111 are disposed. For example, the first arrangement space may be open toward the one surface and the opposite surface of the first housing 113. For example, the first housing 113 may be formed by a bottom surface in which the first electrodes 111 are disposed and a sidewall located on the periphery of the first housing 113 to form a predetermined angle with the bottom surface. The sidewall may be coupled with one side (e.g., a second housing 132) of the main module 130. Furthermore, the sidewall may be formed of an elastic material (e.g., rubber or silicone).

According to some embodiments, the first housing 113 may include an attachment means (e.g., an attachment tape) disposed on at least part of the remaining portion (e.g., the bottom surface of the first housing 113) other than the first arrangement space. For example, as the attachment means is disposed on the one surface of the first housing 113, the first housing 113 may allow the first electrodes 111 to be brought into direct contact with the user's body.

According to an embodiment, one surface of the main module 130 may be coupled to the pad module 110. For example, a plurality of second electrodes 131 and a plurality of magnetic bodies 134 of the main module 130 may be disposed in the second housing 132.

According to an embodiment, at least parts of the second electrodes 131 may be exposed through the one surface of the main module 130. The second electrodes 131 may be brought into electrical contact with the first electrodes 111 so as to face in a second direction (e.g., a lower direction) from a first direction (e.g., an upper direction). According to various embodiments, the second electrodes 131 may receive bio-signals (e.g., action currents) of the user from the first electrodes 111.

According to an embodiment, the second housing 132 may be coupled with the first housing 113 so as to face in the second direction (e.g., the lower direction) from the first direction (e.g., the upper direction). The second housing 132 may form a second arrangement space such that the plurality of second electrodes 131 and the plurality of magnetic bodies 134 are disposed in corresponding positions. For example, the second arrangement space may be open toward at least one surface of the second housing 132. The second housing 132 may include a bottom surface in which the second electrodes 131 are disposed and a cover protruding in a direction (e.g., the upper direction) opposite to the bottom surface. According to various embodiments, the second housing 132 may be provided in a form in which the bottom surface and the cover are separable.

According to some embodiments, in a case where the first electrodes 111 and the second electrodes 131 are brought into contact with each other by an attraction force of the magnetic bodies 134, the second housing 132 may be coupled such that the periphery of the second housing 132 is engaged with the periphery of the first housing 113. The periphery of the second housing 132 may be inserted into the periphery of the first housing 113. The periphery of the second housing 132 may be formed of an elastic material (e.g., rubber or silicone).

According to an embodiment, the magnetic bodies 134 may be disposed in the second housing 132 to correspond to the positions of the second electrodes 131. For example, the magnetic bodies 134 may be disposed on an opposite surface of the second housing 132 to correspond to the positions of the second electrodes 131. According to various embodiments, the magnetic bodies 134 may allow the first electrodes 111 and the second electrodes 131 to be brought into contact with each other by a magnetic force (e.g., an attraction force).

Figure 2:
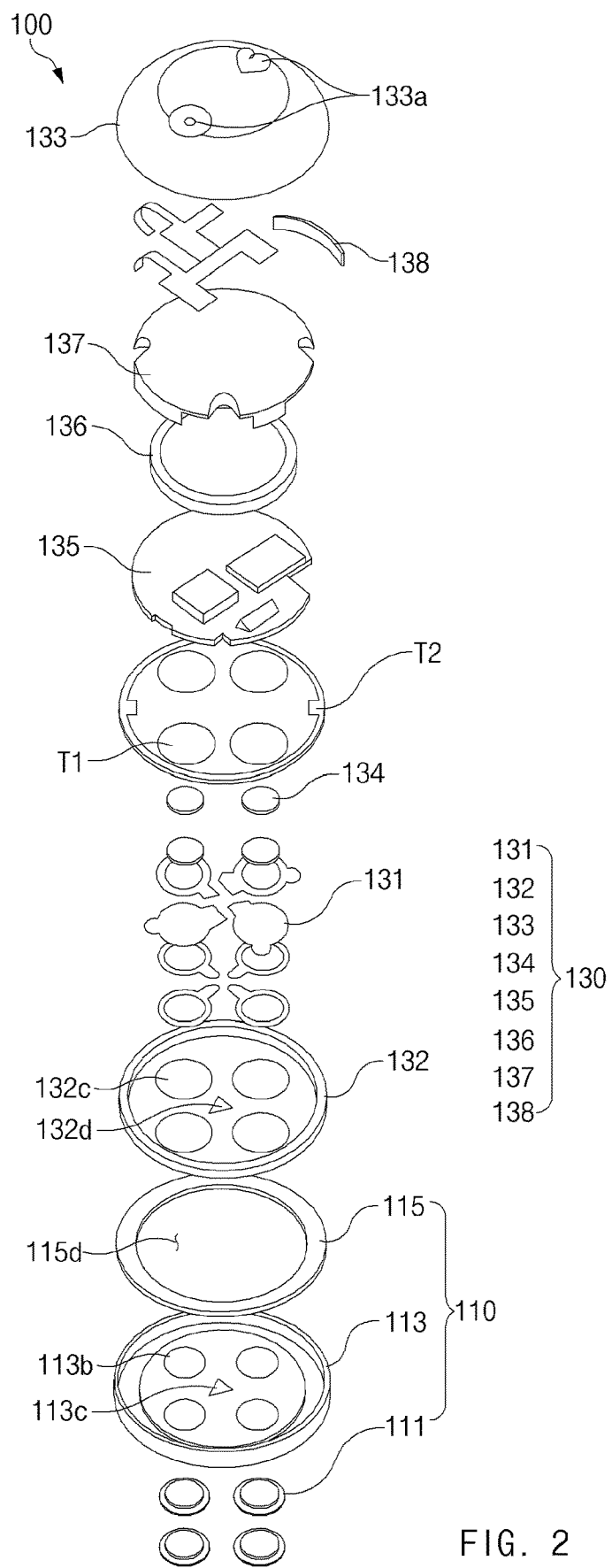
FIG. 2 illustrates an exploded perspective view of the electronic device according to an embodiment.

FIG. 2 illustrates an exploded perspective view of the electronic device according to an embodiment. At least one of components of the electronic device 100 illustrated in FIG. 2 may be the same as, or similar to, at least one of the components of the electronic device 100 illustrated in FIG. 1, and repetitive descriptions will hereinafter be omitted.

Referring to FIG. 2, the electronic device 100 according to an embodiment may include different components in the pad module 110 and the main module 130.

According to an embodiment, the pad module 110 may include at least one of the first electrodes 111, the first housing 113, and a packing member 115.

According to an embodiment, the first electrodes 111 may be disposed in the first housing 113 so as to be exposed through at least parts of the first housing 113. The plurality of first electrodes 111 may be disposed to form corresponding pairs depending on positions in which the first electrodes 111 are brought into contact with the user's body. For example, two first electrodes 111 corresponding to each other may be disposed in different positions to form a pair.

According to an embodiment, the first housing 113 may include at least one of first openings 113b and a first guide 113c.

According to an embodiment, the first openings 113b may form the first arrangement space (e.g., the bottom surface of the first housing 113) in the first housing 113. At least parts of the first electrodes 111 may be disposed in the first openings 113b. For example, flanges of the first electrodes 111 may be mounted on the peripheries of the first openings 113b, and central portions of the first electrodes 111 may be disposed to be exposed through the first openings 113b. The first openings 113b may have a shape corresponding to the shape of the first electrodes 111. For example, in a case where the first electrodes 111 have a circular or spherical shape, the first openings 113b may have a circular shape. According to various embodiments, as many first openings 113b as the first electrodes 111 may be formed.

According to an embodiment, the first guide 113c may be formed on at least the opposite surface (e.g., the upper surface) of the first housing 113. The first guide 113c may include at least three first sides. For example, the first guide 113c may correspond to a triangular recess facing in the second direction (e.g., the lower direction) (or a protrusion facing in the first direction (e.g., the upper direction)).

According to an embodiment, the packing member 115 may be disposed on the periphery of the inside of the first housing 113. For example, the packing member 115 may make contact with the periphery of the inside of the first housing 113 to form a gap. The packing member 115 may be formed in a ring or strap shape. According to various embodiments, the packing member 115 may be formed of an elastic material (e.g., rubber or silicone).

According to some embodiments, the packing member 115 may include a second opening 115d in the center thereof. For example, the second opening 115d may receive the plurality of first openings 113b. For example, the second opening 115d may allow the first electrodes 111 exposed through the first openings 113b to pass through the packing member 115 and make contact with the second electrodes 131.

According to an embodiment, the main module 130 may include at least one of the second electrodes 131, the second housing 132, a third housing 133, the magnetic bodies 134, a controller 135, a power supply 136, a bracket 137, and an antenna 138.

According to an embodiment, the second electrodes 131 may be disposed in one surface (e.g., the bottom surface) of the second housing 132 so as to be exposed through at least part of the second housing 132. The peripheries of the second electrodes 131 may protrude to face in the first direction (e.g., the upper direction), and the magnetic bodies 134 may be seated on the upper surfaces of the second electrodes 131. At least parts of the second electrodes 131 may pass through the second opening 115d and may be brought into contact with the first electrodes 111. As many second electrodes 131 as the first electrodes 111 may be disposed. According to various embodiments, the second electrodes 131 may receive bio-signals (e.g., action currents) of the user from the first electrodes 111.

According to an embodiment, the second housing 132 may include at least one of third openings 132c and a second guide 132d.

According to an embodiment, the third openings 132c may form the second arrangement space (e.g., the bottom surface of the second housing 132) in the second housing 132. For example, at least parts of the second electrodes 131 may be disposed in the third openings 132c. For example, flanges of the second electrodes 131 may be mounted on the peripheries of the third openings 132c, and central portions of the second electrodes 131 may be disposed to be exposed through the third openings 132c. The third openings 132c may have a shape corresponding to the shape of the second electrodes 131. For example, in a case where the second electrodes 131 have a circular or spherical shape, the third openings 132c may have a circular shape. According to various embodiments, as many third openings 132c as the second electrodes 131 may be formed.

According to an embodiment, the second guide 132d may be formed on one surface (e.g., the bottom surface) of the second housing 132. The second guide 132d may include at least three second sides corresponding to the first sides included in the first guide 113c. For example, the second guide 132d may correspond to a triangular protrusion facing in the second direction (e.g., the lower direction) (or a recess facing in the first direction (e.g., the upper direction)). According to various embodiments, in a case where the second guide 132*d* is engaged with the first guide 113*c*, the positions of the first electrodes 111 and the second electrodes 131 may be aligned. For example, in a case where an impact is applied to the main module 130 (or, the pad module 110), the second guide 132*d* engaged with the first guide 113*c* may fix the positions of the first electrodes 111 and the second electrodes 131 to prevent misalignment of the first electrodes 111 and the second electrodes 131. According to various embodiments, in the case where the second guide 132*d* is engaged with the first guide 113*c*, the second guide 132*d* may guide a direction in which the first housing 113 and the second housing 132 are coupled.

According to an embodiment, the third housing 133 may be coupled with the second housing 132 to face in the second direction (e.g., the lower direction) from the first direction (e.g., the upper direction). The third housing 133 may be formed of a cover, the central portion of which protrudes in the first direction (e.g., the upper direction). The third housing 133 may cover the main module 130 from the first direction (e.g., the upper direction). According to various embodiments, the third housing 133 may be coupled with the second housing 132 as a separate component separated from the second housing 132. According to various embodiments, the third housing 133 may be integrated with the second housing 132 to form a single housing.

According to some embodiments, the third housing 133 may include a user interface 133*a*. For example, the user interface 133*a* may be concavely disposed toward the inside of the third housing 133. Physical contact applied to the third housing 133 may not be transmitted to the user interface 133*a* having a concave shape. According to various embodiments, the user interface 133*a* may include a power button to operate the main module 130. According to another embodiment, the user interface 133*a* may allow an operational state (e.g., ON or OFF) of the electronic device 100 to be displayed to the outside.

According to an embodiment, the magnetic bodies 134 may be disposed to correspond to the positions of the second electrodes 131. For example, one surface (e.g., a bottom surface) of each of the magnetic bodies 134 may be disposed on an upper surface of the corresponding second electrode 131. The positions of the magnetic bodies 134 may be fixed by the peripheries of the second electrodes 131. The magnetic bodies 134 may have a magnetic force (e.g., an attraction force).

According to an embodiment, the controller 135 may be disposed between the second housing 132 and the third housing 133. The controller 135 may be disposed on a printed circuit board. The controller 135 may control at least some functions (e.g., electrocardiogram recording) of the main module 130. According to various embodiments, the controller 135 may receive an operating instruction from the user interface 133*a* and may perform control such that at least some functions (e.g., electrocardiogram recording) of the main module 130 are executed depending on executive instructions transferred from a user terminal (e.g., a smartphone or a computer terminal for a medical purpose).

According to an embodiment, the power supply 136 may be operatively connected with at least some components (e.g., the controller 135) of the main module 130. For example, the power supply 136 may supply power to operate and/or execute the main module 130. For example, the power supply 136 may include a battery.

According to an embodiment, in a case where the second housing 132 and the third housing 133 are distinguished from each other, the bracket 137 may be disposed between the second housing 132 and the third housing 133. For example, the bracket 137 may connect the second housing 132 and the third housing 133 separated from each other. According to various embodiments, in a case where the second housing 132 and the third housing 133 are implemented with a single housing, the bracket 137 may be omitted from the main module 130.

According to an embodiment, the antenna 138 may be operatively connected with at least some components (e.g., the controller 135) of the main module 130. For example, the main module 130 may establish a communication channel with a user terminal (e.g., a smartphone) through the antenna 138. For example, the antenna 138 may receive an executive instruction (e.g., execution of electrocardiogram recording) that is transferred from the user terminal to the main module 130. In another example, the antenna 138 may provide at least one piece of biometric information (e.g., an electrocardiogram) from the main module 130 to the user terminal.

According to various embodiments, the main module 130 may further include a first adhesive member T1 and a second adhesive member T2.

According to an embodiment, the first adhesive member T1 may be disposed on an opposite surface of each of the magnetic bodies 134. For example, the first adhesive member T1 may bond the magnetic body 134 and at least part of the corresponding second electrode 131. For example, the first adhesive member T1 may be disposed on the magnetic body 134 in the first direction (e.g., the upper direction) and may bond the upper surface of the magnetic body 134 and the periphery of the second electrode 131. According to various embodiments, at least part of the periphery of the first adhesive member T1 may be bonded to the periphery of the third opening 132*c*. For example, the first adhesive member T1 may be bonded to the periphery of the third opening 132*c* to allow the second electrode 131 to be disposed in the third opening 132*c*.

According to an embodiment, the second adhesive member T2 may be disposed between the second housing 132 and the third housing 133. For example, the second adhesive member T2 may have an adhesive property and may bond the second housing 132 and at least part of the third housing 133. For example, the second adhesive member T2 may vertically bond the periphery of the second housing 132 and the periphery of the third housing 133 to prevent a movement of the second housing 132 and the third housing 133.

Figure 3:
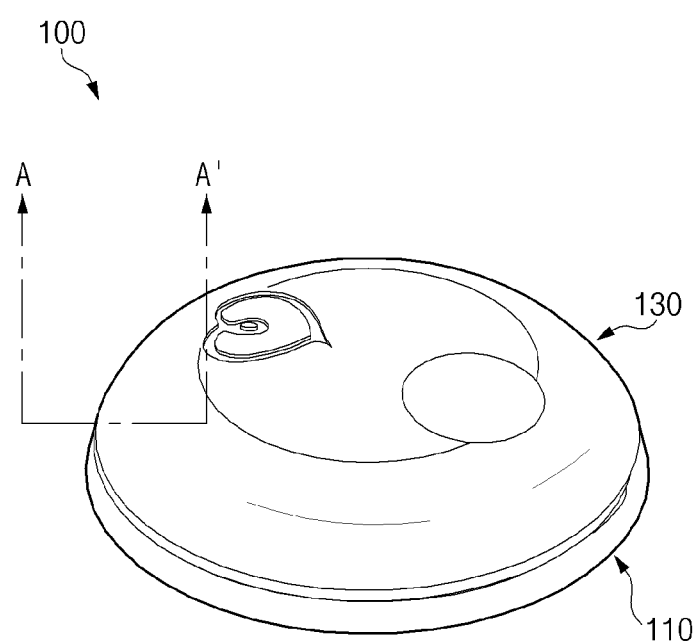
FIG. 3 illustrates a view of a front side of the electronic device according to an embodiment.
Figure 4:
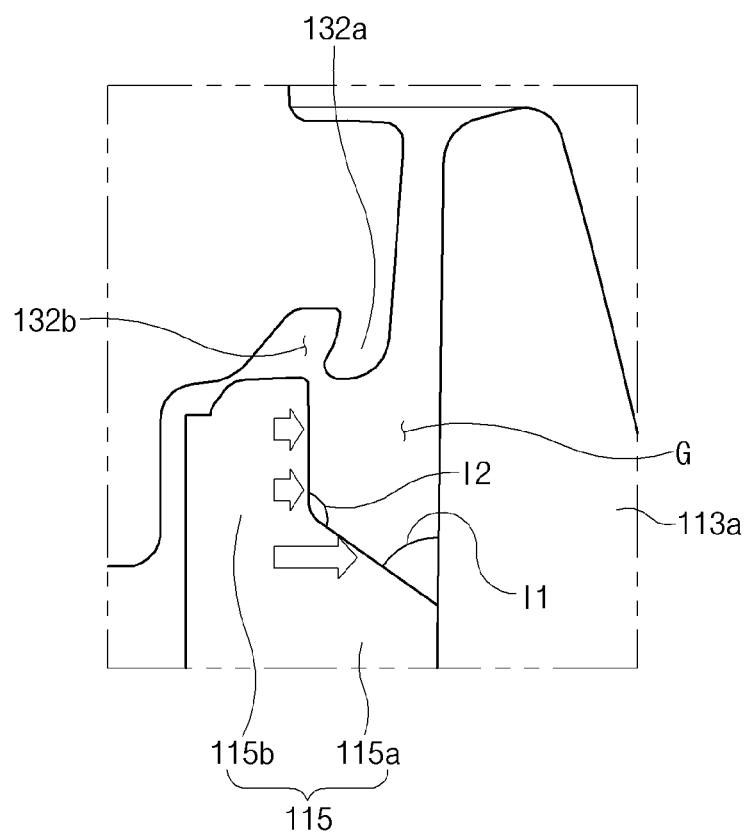
FIG. 4 illustrates a sectional view taken along line A-A' of FIG. 3 according to an embodiment.

FIG. 3 illustrates a view of a front side of the electronic device according to an embodiment. FIG. 4 illustrates a sectional view taken along line A-A' of FIG. 3 according to an embodiment. At least one of components of the electronic device 100 illustrated in FIG. 3 and/or FIG. 4 may be the same as, or similar to, at least one of the components of the electronic device 100 illustrated in FIG. 1 and/or FIG. 2, and repetitive descriptions will hereinafter be omitted.

Referring to FIGS. 3 and 4, in a case where first electrodes (e.g., the first electrodes 111 of FIG. 1) and second electrodes (e.g., the second electrodes 131 of FIG. 1) are brought into contact with each other by an attraction force of magnetic bodies (e.g., the magnetic bodies 134 of FIG. 1), the electronic device 100 according to an embodiment may be switched to a state in which the pad module 110 and the main module 130 are coupled.

According to an embodiment, a first housing (e.g., the first housing 113 of FIG. 1) may include a first sidewall 113*a*. For example, the first sidewall 113*a* may be formed on the periphery of the first housing (e.g., the first housing 113 of FIG. 1).

According to an embodiment, the pad module 110 may further include the packing member 115. For example, the packing member 115 may be disposed on the periphery of the inside of the first sidewall 113a.

According to an embodiment, the packing member 115 may include a second sidewall 115a and a third sidewall 115b.

According to an embodiment, the second sidewall 115a may be formed on the periphery of the packing member 115. For example, the second sidewall 115a may be disposed to be brought into close contact with the inside of the first sidewall 113a. According to some embodiments, the second sidewall 115a may form a first included angle I1, which is an acute angle, between the first sidewall 113a and the second sidewall 115a. For example, the first included angle I1 may allow a gap G to be formed between the first sidewall 113a and the third sidewall 115b.

According to an embodiment, the third sidewall 115b may be disposed on the periphery of the inside of the packing member 115 and may be formed to have a greater height in the upper direction than the second sidewall 115a. For example, the third sidewall 115b may be formed toward the inside of the packing member 115 from one end of the second sidewall 115a. For example, the third sidewall 115b may further protrude beyond the second sidewall 115a in the first direction (e.g., the upper direction) and may form the gap G between the first sidewall 113a and the third sidewall 115b. According to some embodiments, the third sidewall 115b may form a second included angle I2, which is an obtuse angle, between the second sidewall 115a and the third sidewall 115b. For example, even though an external force (e.g., a force generated from the inside to the outside of the packing member 115) is applied to the third sidewall 115b, the second included angle I2 may distribute the external force by the second included angle I2, thereby reducing shock applied to the packing member 115 and preventing the packing member 115 from being brought into contact with the first sidewall 113a.

According to an embodiment, the second housing 132 may include a protrusion 132a and an insertion groove 132b.

According to an embodiment, at least part of the protrusion 132a may be disposed in the gap G between the packing member 115 and the first sidewall 113a in the case where the first electrodes (e.g., the first electrodes 111 of FIG. 1) and the second electrodes (e.g., the second electrodes 131 of FIG. 1) are brought into contact with each other by the attraction force of the magnetic bodies (e.g., the magnetic bodies 134 of FIG. 1). For example, the protrusion 132a may be disposed to be brought into close contact with the third sidewall 115b. For example, the protrusion 132a may be formed to be curved in the direction in which the third sidewall 115b is located (e.g., from the outside to the inside of the packing member 115).

According to an embodiment, the insertion groove 132b may be formed toward the inside of the second housing 132 from the protrusion 132a. For example, at least part of the third sidewall 115b may be inserted into the insertion groove 132b. According to various embodiments, the third sidewall 115b may be inserted into the insertion groove 132b by an external force, and the insertion groove 132b may allow the external force to be transmitted to the third sidewall 115b.

Figure 5:
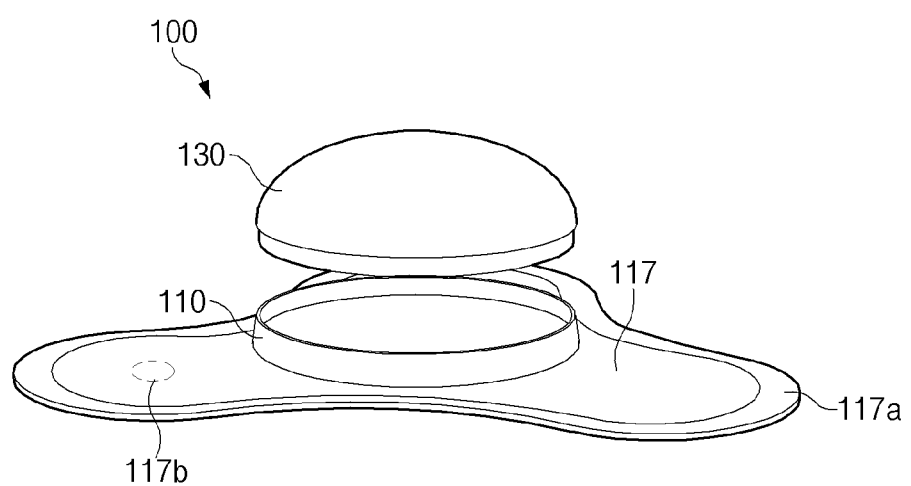
FIG. 5 illustrates a view of the front side of the electronic device according to an embodiment.

FIG. 5 illustrates a view of the front side of the electronic device according to an embodiment.

Referring to FIG. 5, in the electronic device 100 according to an embodiment, the pad module 110 including an attachment member 117 may be coupled to the main module 130.

According to an embodiment, the attachment member 117 may be coupled with at least part of a first housing (e.g., the first housing 113 of FIG. 2) to face in the first direction (e.g., the upper direction) from the second direction (e.g., the lower direction). For example, the attachment member 117 may be disposed on the remaining portion of the first housing (e.g., the first housing 113 of FIG. 2) other than first openings (e.g., the first openings 113b of FIG. 2) in the second direction (e.g., the lower direction). According to an embodiment, the attachment member 117 may be disposed to a range beyond the periphery of the first housing (e.g., the first housing 113 of FIG. 2). For example, the attachment member 117 may include at least one of an attachment surface 117a and a node 117b. According to various embodiments, the attachment member 117 may be separated from, or coupled with, the first housing (e.g., the first housing 113 of FIG. 2).

According to an embodiment, the attachment surface 117a may be formed in the range beyond at least the periphery of the first housing (e.g., the first housing 113 of FIG. 2). For example, the attachment surface 117a may have an adhesive property in the second direction (e.g., the lower direction) and may be attached to the user's body. For example, the attachment surface 117a may allow the pad module 110 to be attached to the user's body. Furthermore, the attachment surface 117a may allow the main module 130 to be coupled to the pad module 110 in a state in which the pad module 110 is attached to the user's upper body.

According to an embodiment, the node 117b may be disposed on at least one side of the attachment surface 117a. For example, the node 117b may be electrically connected with the first electrodes 111. For example, the node 117b may be exposed on the attachment surface 117a in the second direction (e.g., the lower direction), and at least part of the exposed area may be brought into contact with the user's body. According to various embodiments, as the node 117b is brought into direct contact with the user's body, the first electrodes 111 may be brought into indirect contact with the user's body. According to various embodiments, the node 117b may be formed of a material (e.g., brass) that is the same as, or similar to, that of at least one of first electrodes (e.g., the first electrodes 111 of FIG. 2) and second electrodes (e.g., the second electrodes 131 of FIG. 2).

Figure 6:
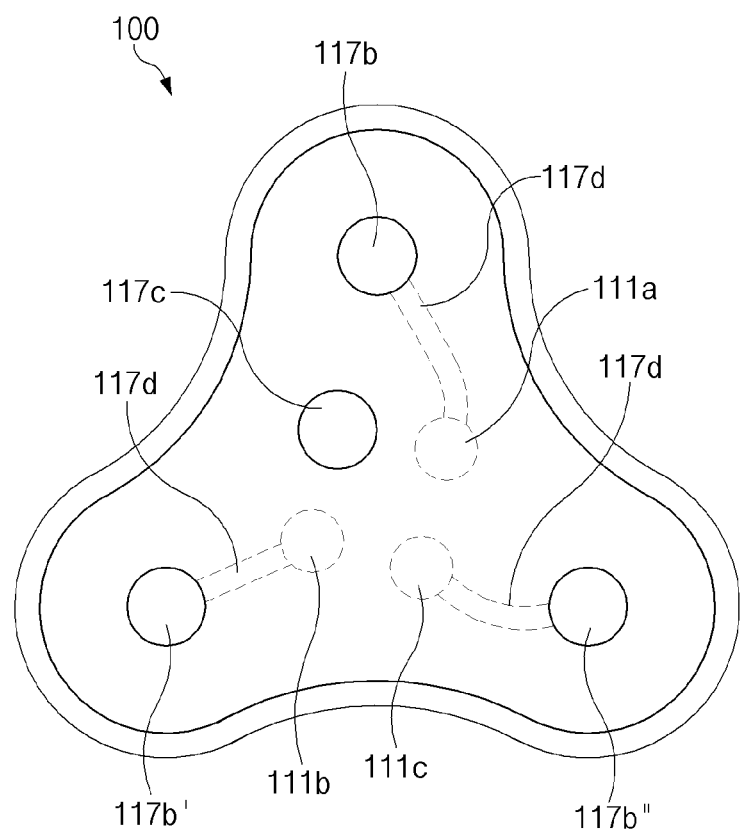
FIG. 6 illustrates a view of the rear side of the electronic device according to an embodiment.

FIG. 6 illustrates a view of the rear side of the electronic device according to an embodiment.

Referring to FIG. 6, in the electronic device 100 according to an embodiment, nodes 117b, 117b', and 117b" may be disposed on at least one side of the attachment member 117 to correspond to the first electrodes 111.

According to an embodiment, the electronic device 100 may include a plurality of first electrodes (at least two of 111a, 111b, and 111c) disposed in the first housing 113. For example, the plurality of nodes (at least two of 117b, 117b', and 117b") of the attachment member 117 may be paired with the plurality of first electrodes (at least two of 111a, 111b, and 111c). For example, one first electrode 111a may be electrically connected with one node 117b.

According to an embodiment, the electronic device 100 may include a reference 117c disposed on another side of the attachment member 117. For example, the reference 117c may be disposed to correspond to first electrodes (e.g., the first electrodes 111 of FIG. 2) other than the first electrodes 111a, 111b, and 111c connected with the nodes 117b, 117b', and 117b". For example, the reference 117c may include a high signal (e.g., 5 V) or a low signal (e.g., 0 V) as a reference for the electrical potential of the electronic device 100.

According to an embodiment, the electronic device 100 may include connecting wires 117d disposed between the plurality of first electrodes (at least two of 111a, 111b, and 111c) and the plurality of nodes (at least two of 117b, 117b', and 117b") that correspond to each other. For example, the connecting wire 117d may electrically connect one first electrode 111a and one node 117b.

Figure 7:
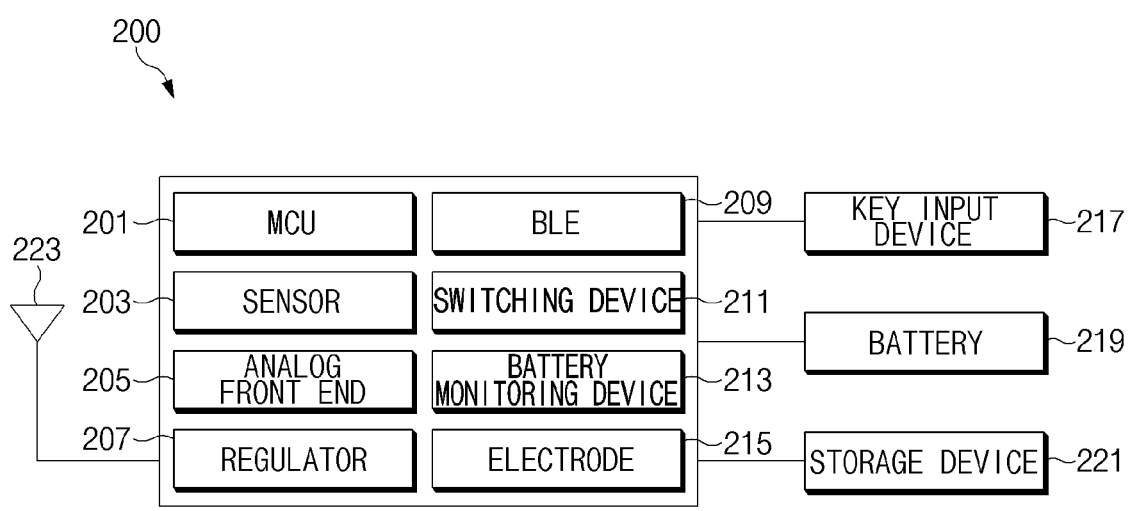
FIG. 7 illustrates a block diagram of an electronic device according to an embodiment.

FIG. 7 illustrates a block diagram of an electronic device according to an embodiment.

Referring to FIG. 7, the electronic device 200 according to an embodiment (e.g., the electronic device 100 of FIG. 1) may include at least one of a micro controller unit (MCU) 201, a sensor 203, an analog front end (AFE) 205, a regulator 207, Bluetooth low energy (BLE) 209, a switching device 211, a battery monitoring device 213, an electrode 215, a key input device 217, a battery 219, a storage device 221, and an antenna 223.

According to an embodiment, the MCU 201 may control at least some components (e.g., the power supply 136 and the antenna 138 of FIG. 2) of the electronic device 200.

According to an embodiment, the sensor 203 (e.g., an acceleration sensor) may measure a movement change (e.g., acceleration) of a user to which the electronic device 200 is attached. For example, the sensor 203 may identify a specific situation (e.g., exercise or sleep) in the user's daily life. For example, the sensor 203 may provide the specific situation depending on the movement change of the user to a user terminal (e.g., a smartphone) to allow the user's biometric information (e.g., electrocardiogram) detected through the electrode 215 to be associated with the specific situation.

According to an embodiment, the sensor 203 (e.g., a Hall sensor) may measure the magnetic force of the electrode 215 (e.g., the first electrodes 111 and the second electrodes 131 of FIG. 1). For example, the sensor 203 may measure the magnetic forces of the first electrodes 111 and the second electrodes 131 in a case where the first electrodes 111 and the second electrodes 131 are brought into contact with each other by magnetic bodies (e.g., 134 of FIG. 1).

According to an embodiment, the analog front end (AFE) 205 may process analog voltage signals for bio-signals (e.g., action currents) of the user obtained through first electrodes (e.g., the first electrodes 111 of FIG. 1) and may digitize and transmit a processed result to the MCU 201.

According to an embodiment, the regulator 207 may convert the power of the battery 219 such that the power of the battery 219 corresponds to the driving voltage of the electronic device 200.

According to an embodiment, in a case where software (e.g., an application) for identifying the user's biometric information (e.g., electrocardiogram) is used in a user terminal (e.g., a smartphone) with which the electronic device 200 establishes a communication channel, the BLE 209 may transmit the biometric information to the user terminal.

According to an embodiment, the switching device 211 (e.g., the user interface 133a of FIG. 2) may determine an operational state (e.g., ON or OFF) of the electronic device 200 depending on an external input (e.g., the user's contact).

According to various embodiments, the switching device 211 (e.g., the user interface 133a of FIG. 2) may control an operational state (e.g., ON or OFF) of the electronic device 200 depending on a signal (e.g., the magnetic force of the electrode 215) that is measured through the sensor 203. For example, in a case where the magnitude of a magnetic force measured through the sensor 203 is greater than or equal to a specified reference value, the switching device 211 may determine that a pad module (e.g., the pad module 110 of FIG. 1) and a main module (e.g., the main module 130 of FIG. 1) are normally coupled, and may switch an operational state of the electronic device 200 to an ON state. In another example, in a case where the magnitude of the measured magnetic force is smaller than the specified reference value, the switching device 211 may provide a guide (e.g., an alarm) to couple the pad module 110 and the main module 130 again, or may switch an operational state of the electronic device 200 to an OFF state.

According to an embodiment, the battery monitoring device 213 may monitor the remaining amount of a charge of the battery 219. For example, in a case where the remaining amount of a charge of the battery 219 is less than or equal to a specified value (e.g., 50%), the battery monitoring device 213 may perform notification (e.g., display a red color) through an indicator (e.g., an LED) depending on the remaining amount of a charge of the battery 219. For example, in a case where the battery 219 is being charged by an external power supply, the battery monitoring device 213 may perform notification (e.g., display a red or blue color) through the indicator (e.g., an LED) depending on the charging of the battery 219.

According to an embodiment, the electrode 215 (e.g., the first electrodes 111 of FIG. 1) may obtain bio-signals (e.g., action currents) generated from the user's body (e.g., heart).

According to an embodiment, the key input device 217 (e.g., a key FPCB) may identify an operational state (ON or OFF) of the electronic device 200. For example, the key input device 217 may be electrically connected with the switching device 211.

According to an embodiment, the battery 219 (e.g., the power supply 136 of FIG. 2) may supply power to operate and/or execute the electronic device 200. For example, the remaining amount of a charge of the battery 219 may be monitored by the battery monitoring device 213. For example, the charging state of the battery 219 may be monitored by the battery monitoring device 213.

According to an embodiment, the storage device 221 (e.g., a memory) may store the user's bio-signals (e.g., action currents) obtained through the first electrodes (e.g., the first electrodes 111 of FIG. 1). For example, the storage device 221 may store the user's bio-signals (e.g., action currents) as biometric information (e.g., electrocardiogram). According to an embodiment, the storage device 221 may additionally store the user's movement change (e.g., acceleration) measured through the sensor 203.

According to an embodiment, the antenna 223 (e.g., the antenna 138 of FIG. 2) may allow the electronic device 200 to establish a communication channel with a user terminal (e.g., a smartphone). For example, the antenna 223 may receive an executive instruction (e.g., execution of electrocardiogram recording) that is transferred from the user terminal to the electronic device 200. In another example, the antenna 223 may provide at least one piece of biometric information (e.g., electrocardiogram or acceleration information) from the electronic device 200 to the user terminal.

According to various embodiments, the electronic device 200 including at least one of the MCU 201, the sensor 203, the analog front end 205, the regulator 207, the BLE 209, the switching device 211, the battery monitoring device 213, the electrode 215, the key input device 217, the battery 219, the storage device 221, and the antenna 223 may have a structure for obtaining approval for a medical device.

Figure 8:
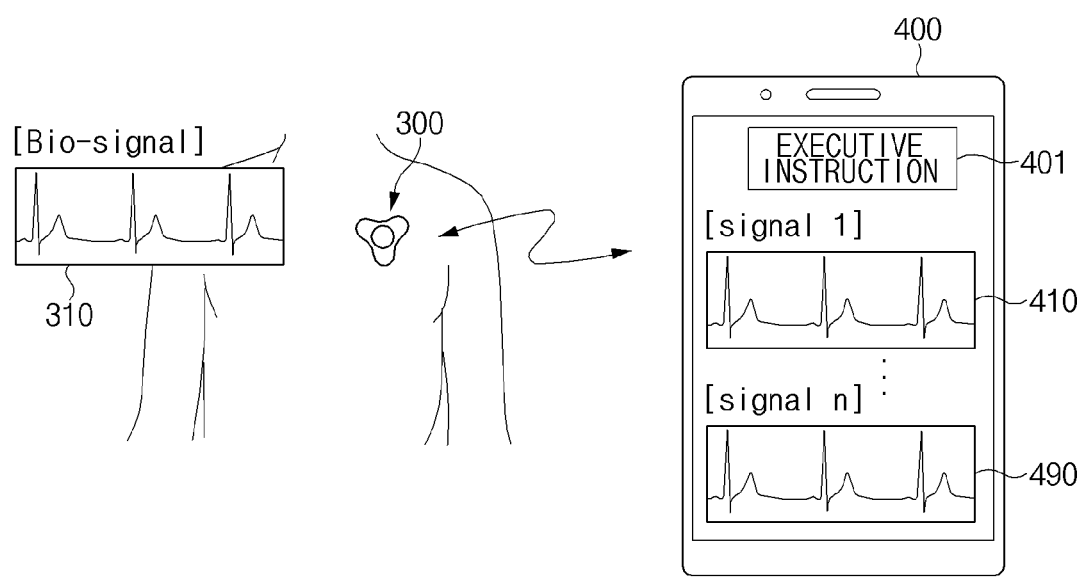
FIG. 8 illustrates a view of an operating environment of an electronic device according to an embodiment.

FIG. 8 illustrates a view of an operating environment of an electronic device according to an embodiment.

Referring to FIG. 8, the electronic device 300 according to an embodiment (e.g., the electronic device 100 of FIG. 1) may be attached to a user's body. For example, first electrodes of the electronic device 300 (e.g., the first electrodes 111 of FIG. 1) may be brought into direct contact with the user's body. In another example, the first electrodes of the electronic device 300 (e.g., the first electrodes 111 of FIG. 6) may be brought into indirect contact with the user's body through a plurality of nodes (e.g., the node 117b of FIG. 6).

According to an embodiment, the electronic device 300 may obtain bio-signals 310 of the user through the first electrodes (e.g., the first electrodes 111 of FIG. 1 or FIG. 6). For example, the electronic device 300 may store the bio-signals 310 obtained from the user as biometric information (e.g., electrocardiogram).

According to an embodiment, a user terminal 400 (e.g., a smartphone) may establish a communication channel with the electronic device 300. The user terminal 400 may receive at least one piece of biometric information via the bio-signals 410 and/or 490 from the electronic device 300 through the communication channel and may display the received biometric information.

According to an embodiment, the user terminal 400 may transmit an executive instruction 401 to the electronic device 300 after the at least one bio-signal 410 or 490 transmitted from the electronic device 300 is displayed. For example, the executive instruction 401 may allow at least some functions (e.g., electrocardiogram recording) of the electronic device 300 to be executed. According to some embodiments, the user terminal 400 may display occurrence of an event on the electronic device 300. For example, the event may include a situation in which no bio-signals (e.g., action currents) are obtained from the electronic device 300. In another example, the event may include a situation in which the remaining amount of a charge of a battery of the electronic device 300 (e.g., the power supply 136 of FIG. 2 or the battery 219 of FIG. 8) is less than or equal to a specified value (e.g., 50%).

According to various embodiments, in a case where the user terminal 400 is managed in a medical institution, the user terminal 400 may collect biometric information (e.g., electrocardiogram) from the electronic device 300 and may analyze the collected biometric information.

According to an embodiment, the user terminal 400 (e.g., a smartphone) may display a plurality of bio-signals 410 and 490 depending on the number of first electrodes (e.g., the first electrodes 111 of FIG. 1) that are disposed in the electronic device 300.

According to the various embodiments described above, an electronic device (e.g., the electronic device 100 of FIG. 1) for supporting measurement of a bio-signal may include a pad module (e.g., the pad module 110 of FIG. 1), at least part of which is attached to a user's body to obtain a bio-signal of the user and a main module (e.g., the main module 130 of FIG. 1) that records the user's bio-signal transferred through the pad module. The pad module may include a plurality of first electrodes (e.g., the first electrodes 111 of FIG. 1) and a first housing (e.g., the first housing 113 of FIG. 1) in which the plurality of first electrodes are disposed. The main module may include a plurality of second electrodes (e.g., the second electrodes 131 of FIG. 1) that make electrical contact with the plurality of first electrodes, a second housing (e.g., the second housing 132 of FIG. 1) in which the plurality of second electrodes are disposed, the second housing being coupled with the first housing in a first direction, and a plurality of magnetic bodies (e.g., the magnetic bodies 134 of FIG. 1) disposed in the second housing to correspond to positions of the plurality of second electrodes, in which the plurality of magnetic bodies allow the plurality of first electrodes and the plurality of second electrodes to be brought into contact with each other by a magnetic force. When the plurality of first electrodes and the plurality of second electrodes are brought into contact with each other by an attraction force of the magnetic bodies, the second housing may be coupled with the first housing such that a periphery of the second housing is engaged with a periphery of the first housing.

According to various embodiments, the pad module may include a packing member (e.g., the packing member 115 of FIG. 4) disposed on a periphery of the inside of a first sidewall (e.g., the first sidewall 113a of FIG. 4) included in the first housing, and the second housing may include a protrusion (e.g., the protrusion 132a of FIG. 4) disposed in a gap (e.g., the gap G of FIG. 4) between the packing member and the first sidewall when the plurality of first electrodes and the plurality of second electrodes are brought into contact with each other by the attraction force of the magnetic bodies.

According to various embodiments, an available space other than a space in which the protrusion is disposed may be formed in the gap.

According to various embodiments, the packing member may include a second sidewall (e.g., the second sidewall 115a of FIG. 4) that makes contact with the inside of the first sidewall and a third sidewall (e.g., the third sidewall 115b of FIG. 4) that is formed toward the inside of the packing member from the second sidewall and that further protrudes in the first direction beyond the second sidewall and forms the gap between the first sidewall and the third sidewall.

According to various embodiments, a first included angle (e.g., the first included angle I1 of FIG. 4) may be formed between the first sidewall and the second sidewall, the first included angle being an acute angle.

According to various embodiments, a second included angle (e.g., the second included angle 12 of FIG. 4) may be formed between the second sidewall and the third sidewall, the second included angle being an obtuse angle.

According to various embodiments, the protrusion may be curved in a direction in which the third sidewall is located.

According to various embodiments, the second housing may include an insertion groove (e.g., the insertion groove 132b of FIG. 4) formed toward the inside of the second housing from the protrusion, at least part of the third sidewall being inserted into the insertion groove.

According to various embodiments, the pad module may include an attachment member (e.g., the attachment member 117 of FIG. 5) coupled with the first housing in a second direction, and the attachment member may include an attachment surface (e.g., the attachment surface 117a of FIG. 5) that has an adhesive property.

According to various embodiments, the attachment member may include a plurality of nodes (e.g., the node 117b of FIG. 5) electrically connected with the plurality of first electrodes and brought into contact with the user's body.

According to various embodiments, the first housing may include a first guide (e.g., the first guide 113c of FIG. 2) that has at least three first sides, and the second housing may include a second guide (e.g., the second guide 132d of FIG. 2) that has at least three second sides corresponding to the at least three first sides.

According to various embodiments, the first guide, when engaged with the second guide, may allow the plurality of first electrodes and the plurality of second electrodes to be brought into contact with each other by the attraction force of the magnetic bodies.

According to various embodiments, the main module may include a third housing (e.g., the third housing 133 of FIG. 2) coupled with the second housing in the first direction, and the third housing may include a user interface (e.g., the user interface 133a of FIG. 2) concavely disposed toward the inside of the third housing.

According to various embodiments, the main module may communicate with a user terminal such that the bio-signal of the user is displayed on the user terminal.

According to various embodiments, the main module may record the bio-signal of the user depending on an executive instruction input from a user terminal.

According to the various embodiments described above, an electronic device (e.g., the electronic device 100 of FIG. 1) for supporting measurement of a bio-signal may include a pad module (e.g., the pad module 110 of FIG. 1), at least part of which is attached to a user's body to obtain a bio-signal of the user and a main module (e.g., the main module 130 of FIG. 1) that records the user's bio-signal transferred through the pad module. The pad module may include a plurality of first electrodes (the first electrodes 111 of FIG. 1), a first housing (e.g., the first housing 113 of FIG. 1) in which the plurality of first electrodes are disposed, and a packing member (e.g., the packing member 115 of FIG. 4) disposed on a periphery of the inside of a first sidewall (e.g., the first sidewall 113a of FIG. 4) included in the first housing. The main module may include a plurality of second electrodes (e.g., the second electrodes 131 of FIG. 1) that make electrical contact with the plurality of first electrodes, a second housing (e.g., the second housing 132 of FIG. 1) in which the plurality of second electrodes are disposed, the second housing being coupled with the first housing in a first direction, and a plurality of magnetic bodies (e.g., the magnetic bodies 134 of FIG. 1) disposed in the second housing to correspond to positions of the plurality of second electrodes, in which the plurality of magnetic bodies allow the plurality of first electrodes and the plurality of second electrodes to be brought into contact with each other by a magnetic force. The second housing may include a protrusion (e.g., the protrusion 132a of FIG. 4) disposed in a gap (e.g., the gap G of FIG. 4) between the packing member and the first sidewall when the plurality of first electrodes and the plurality of second electrodes are brought into contact with each other by an attraction force of the magnetic bodies.

According to various embodiments, an available space other than a space in which the protrusion is disposed may be formed in the gap.

According to various embodiments, the packing member may include a second sidewall (e.g., the second sidewall 115a of FIG. 4) that makes contact with the inside of the first sidewall and a third sidewall (e.g., the third sidewall 115b of FIG. 4) that is formed toward the inside of the packing member from the second sidewall and that further protrudes in the first direction beyond the second sidewall and forms the gap between the first sidewall and the third sidewall.

According to various embodiments, a first included angle (e.g., the first included angle I1 of FIG. 4) may be formed between the first sidewall and the second sidewall, the first included angle being an acute angle.

According to various embodiments, a second included angle (e.g., the second included angle 12 of FIG. 4) may be formed between the second sidewall and the third sidewall, the second included angle being an obtuse angle.

Figure 9:
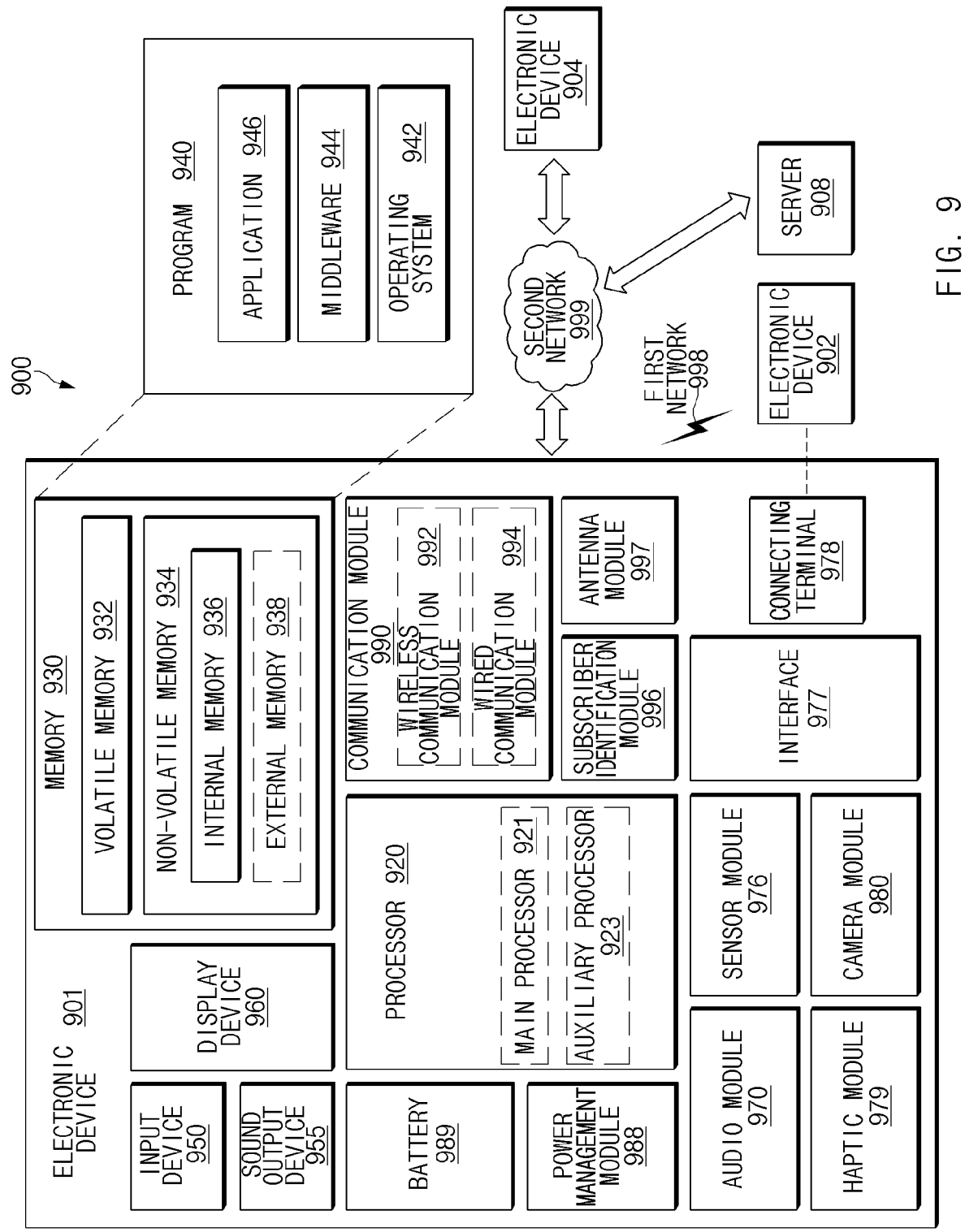
FIG. 9 illustrates a block diagram of an electronic device in a network environment according to various embodiments.

FIG. 9 illustrates a block diagram of an electronic device 901 in a network environment 900 according to various embodiments.

Referring to FIG. 9, the electronic device 901 in the network environment 900 may communicate with an electronic device 902 via a first network 998 (e.g., a short-range wireless communication network), or an electronic device 904 or a server 908 via a second network 999 (e.g., a long-range wireless communication network). According to an embodiment, the electronic device 901 may communicate with the electronic device 904 via the server 908. According to an embodiment, the electronic device 901 may include a processor 920, memory 930, an input device 950, a sound output device 955, a display device 960, an audio module 970, a sensor module 976, an interface 977, a haptic module 979, a camera module 980, a power management module 988, a battery 989, a communication module 990, a subscriber identification module(SIM) 996, or an antenna module 997. In some embodiments, at least one (e.g., the display device 960 or the camera module 980) of the components may be omitted from the electronic device 901, or one or more other components may be added in the electronic device 901. In some embodiments, some of the components may be implemented as single integrated circuitry. For example, the sensor module 976 (e.g., a fingerprint sensor, an iris sensor, or an illuminance sensor) may be implemented as embedded in the display device 960 (e.g., a display).

The processor 920 may execute, for example, software (e.g., a program 940) to control at least one other component (e.g., a hardware or software component) of the electronic device 901 coupled with the processor 920, and may perform various data processing or computation. According to one embodiment, as at least part of the data processing or computation, the processor 920 may load a command or data received from another component (e.g., the sensor module 976 or the communication module 990) in volatile memory 932, process the command or the data stored in the volatile memory 932, and store resulting data in non-volatile memory 934. According to an embodiment, the processor 920 may include a main processor 921 (e.g., a central processing unit (CPU) or an application processor (AP)), and an auxiliary processor 923 (e.g., a graphics processing unit (GPU), an image signal processor (ISP), a sensor hub processor, or a communication processor (CP)) that is operable independently from, or in conjunction with, the main processor 921. Additionally or alternatively, the auxiliary processor 923 may be adapted to consume less power than the main processor 921, or to be specific to a specified function. The auxiliary processor 923 may be implemented as separate from, or as part of the main processor 921.

The auxiliary processor 923 may control at least some of functions or states related to at least one component (e.g., the display device 960, the sensor module 976, or the communication module 990) among the components of the electronic device 901, instead of the main processor 921 while the main processor 921 is in an inactive (e.g., sleep) state, or together with the main processor 921 while the main processor 921 is in an active state (e.g., executing an application). According to an embodiment, the auxiliary processor 923 (e.g., an image signal processor or a communication processor) may be implemented as part of another component (e.g., the camera module 980 or the communication module 990) functionally related to the auxiliary processor 923.

The memory 930 may store various data used by at least one component (e.g., the processor 920 or the sensor module 976) of the electronic device 901. The various data may include, for example, software (e.g., the program 940) and input data or output data for a command related thereto. The memory 930 may include the volatile memory 932 or the non-volatile memory 934.

The program 940 may be stored in the memory 930 as software, and may include, for example, an operating system (OS) 942, middleware 944, or an application 946.

The input device 950 may receive a command or data to be used by other component (e.g., the processor 920) of the electronic device 901, from the outside (e.g., a user) of the electronic device 901. The input device 950 may include, for example, a microphone, a mouse, a keyboard, or a digital pen (e.g., a stylus pen).

The sound output device 955 may output sound signals to the outside of the electronic device 901. The sound output device 955 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 960 may visually provide information to the outside (e.g., a user) of the electronic device 901. The display device 960 may include, for example, a display, a hologram device, or a projector and control circuitry to control a corresponding one of the display, hologram device, and projector. According to an embodiment, the display device 960 may include touch circuitry adapted to detect a touch, or sensor circuitry (e.g., a pressure sensor) adapted to measure the intensity of force incurred by the touch.

The audio module 970 may convert a sound into an electrical signal and vice versa. According to an embodiment, the audio module 970 may obtain the sound via the input device 950, or output the sound via the sound output device 955 or a headphone of an external electronic device (e.g., an electronic device 902) directly (e.g., wiredly) or wirelessly coupled with the electronic device 901.

The sensor module 976 may detect an operational state (e.g., power or temperature) of the electronic device 901 or an environmental state (e.g., a state of a user) external to the electronic device 901, and then generate an electrical signal or data value corresponding to the detected state. According to an embodiment, the sensor module 976 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 977 may support one or more specified protocols to be used for the electronic device 901 to be coupled with the external electronic device (e.g., the electronic device 902) directly (e.g., wiredly) or wirelessly. According to an embodiment, the interface 977 may include, for example, a high definition multimedia interface (HDMI), a universal serial bus (USB) interface, a secure digital (SD) card interface, or an audio interface.

A connecting terminal 978 may include a connector via which the electronic device 901 may be physically connected with the external electronic device (e.g., the electronic device 902). According to an embodiment, the connecting terminal 978 may include, for example, a HDMI connector, a USB connector, a SD card connector, or an audio connector (e.g., a headphone connector).

The haptic module 979 may convert an electrical signal into a mechanical stimulus (e.g., a vibration or a movement) or electrical stimulus which may be recognized by a user via his tactile sensation or kinesthetic sensation. According to an embodiment, the haptic module 979 may include, for example, a motor, a piezoelectric element, or an electric stimulator.

The camera module 980 may capture a still image or moving images. According to an embodiment, the camera module 980 may include one or more lenses, image sensors, image signal processors, or flashes.

The power management module 988 may manage power supplied to the electronic device 901. According to one embodiment, the power management module 988 may be implemented as at least part of, for example, a power management integrated circuit (PMIC).

The battery 989 may supply power to at least one component of the electronic device 901. According to an embodiment, the battery 989 may include, for example, a primary cell which is not rechargeable, a secondary cell which is rechargeable, or a fuel cell.

The communication module 990 may support establishing a direct (e.g., wired) communication channel or a wireless communication channel between the electronic device 901 and the external electronic device (e.g., the electronic device 902, the electronic device 904, or the server 908) and performing communication via the established communication channel. The communication module 990 may include one or more communication processors that are operable independently from the processor 920 (e.g., the application processor (AP)) and supports a direct (e.g., wired) communication or a wireless communication. According to an embodiment, the communication module 990 may include a wireless communication module 992 (e.g., a cellular communication module, a short-range wireless communication module, or a global navigation satellite system (GNSS) communication module) or a wired communication module 994 (e.g., a local area network (LAN) communication module or a power line communication (PLC) module). A corresponding one of these communication modules may communicate with the external electronic device via the first network 998 (e.g., a short-range communication network, such as BLUETOOTH, wireless-fidelity (Wi-Fi) direct, or infrared data association (IrDA)) or the second network 999 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 992 may identify and authenticate the electronic device 901 in a communication network, such as the first network 998 or the second network 999, using subscriber information (e.g., international mobile subscriber identity (IMSI)) stored in the subscriber identification module 996.

The antenna module 997 may transmit or receive a signal or power to or from the outside (e.g., the external electronic device) of the electronic device 901. According to an embodiment, the antenna module 997 may include an antenna including a radiating element composed of a conductive material or a conductive pattern formed in or on a substrate (e.g., PCB). According to an embodiment, the antenna module 997 may include a plurality of antennas. In such a case, at least one antenna appropriate for a communication scheme used in the communication network, such as the first network 998 or the second network 999, may be selected, for example, by the communication module 990 (e.g., the wireless communication module 992) from the plurality of antennas. The signal or the power may then be transmitted or received between the communication module 990 and the external electronic device via the selected at least one antenna. According to an embodiment, another component (e.g., a radio frequency integrated circuit (RFIC)) other than the radiating element may be additionally formed as part of the antenna module 997.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 901 and the external electronic device 904 via the server 908 coupled with the second network 999. Each of the electronic devices 902 and 904 may be a device of a same type as, or a different type, from the electronic device 901. According to an embodiment, all or some of operations to be executed at the electronic device 901 may be executed at one or more of the external electronic devices 902, 904, or 908. For example, if the electronic device 901 should perform a function or a service automatically, or in response to a request from a user or another device, the electronic device 901, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 901. The electronic device 901 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 940) including one or more instructions that are stored in a storage medium (e.g., internal memory 936 or external memory 938) that is readable by a machine (e.g., the electronic device 100). For example, a processor (e.g., the processor 920) of the machine (e.g., the electronic device 100) may invoke at least one of the one or more instructions stored in the storage medium, and execute the instructions, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PLAYSTORE), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to the various embodiments of the disclosure, the electronic device for measuring bio-signals may have improved waterproofing performance (e.g., IPX7).

Furthermore, according to the various embodiments of the disclosure, a module capable of recording an electrocardiogram is provided to an electrode pad in a removable form. Accordingly, degradation in attachment performance of the electrode pad may be prevented, and the electrocardiogram recording module may be reused.

In addition, the disclosure may provide various effects that are directly or indirectly recognized.

While the disclosure has been shown and described with reference to various embodiments thereof, it will be understood by those skilled in the art that various changes in form and details may be made therein without departing from the spirit and scope of the disclosure as defined by the appended claims and their equivalents.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device for supporting bio-signal measurement, the electronic device comprising:
   a pad module, at least part of the pad module is adapted to be attached to a user to obtain a bio-signal of the user, wherein the pad module includes:
   a plurality of first electrodes, and a first housing in which the plurality of first electrodes are disposed; and
   a main module configured to record the bio-signal of the user that is transferred through the pad module, wherein the main module includes:
   a plurality of second electrodes configured to make electrical contact with the plurality of first electrodes,
   a second housing in which the plurality of second electrodes are disposed, the second housing being coupled with the first housing in a first direction, and
   a plurality of magnetic bodies disposed in the second housing to correspond to positions of the plurality of second electrodes, wherein the plurality of magnetic bodies allow the plurality of first electrodes and the plurality of second electrodes to be brought into contact with each other by a magnetic force,
   wherein when the plurality of first electrodes and the plurality of second electrodes are brought into contact with each other by an attraction force of the magnetic bodies, the second housing is coupled with the first housing and a periphery of the second housing is engaged with a periphery of the first housing,
   wherein the first housing includes a first guide and the second housing includes a second guide corresponding to the first guide, and
   wherein the first guide includes a protrusion or a recess, and the second guide includes the protrusion or the recess not included in the first guide.

2. The electronic device of claim 1, wherein:
   the pad module includes a packing member disposed on a periphery of an inside of a first sidewall included in the first housing, and
   the second housing includes a protrusion disposed in a gap between the packing member and the first sidewall when the plurality of first electrodes and the plurality of second electrodes are brought into contact with each other by the attraction force of the magnetic bodies.

3. The electronic device of claim 2, wherein an available space other than a space in which the protrusion is disposed is formed in the gap.

4. The electronic device of claim 2, wherein the packing member includes:
   a second sidewall configured to make contact with the inside of the first sidewall; and
   a third sidewall formed toward an inside of the packing member from the second sidewall and configured to form the gap between the first sidewall and the third sidewall, the third sidewall further protruding in the first direction beyond the second sidewall.

5. The electronic device of claim 4, wherein a first included angle is formed between the first sidewall and the second sidewall, the first included angle being an acute angle.

6. The electronic device of claim 4, wherein a second included angle is formed between the second sidewall and the third sidewall, the second included angle being an obtuse angle.

7. The electronic device of claim 4, wherein the protrusion is curved in a direction in which the third sidewall is located.

8. The electronic device of claim 4, wherein the second housing includes an insertion groove formed toward an inside of the second housing from the protrusion, at least part of the third sidewall being inserted into the insertion groove.

9. The electronic device of claim 1, wherein:
   the pad module includes an attachment member coupled with the first housing in a second direction, and
   the attachment member includes an attachment surface including an adhesive property.

10. The electronic device of claim 9, wherein the attachment member includes a plurality of nodes electrically connected with the plurality of first electrodes and brought into contact with the user.

11. The electronic device of claim 1, wherein:
    the first guide includes at least three first sides; and
    the second guide includes at least three second sides corresponding to the at least three first sides.

12. The electronic device of claim 1, wherein the first guide, when engaged with the second guide, allows the plurality of first electrodes and the plurality of second electrodes to be brought into contact with each other by the attraction force of the magnetic bodies.

13. The electronic device of claim 1, wherein:
    the main module includes a third housing coupled with the second housing in the first direction, and
    the third housing includes a user interface concavely disposed toward an inside of the third housing.

14. The electronic device of claim 1, further comprising:
    a communication module; and
    wherein the main module communicates provide the bio-signal of the user to an external electronic device through the communication module such that the bio-signal of the user is displayed on the external electronic device.

15. The electronic device of claim 1, further comprising:
    a communication module; and
    wherein the main module records the bio-signal of the user depending on an executive instruction received from an external electronic device.

16. An electronic device for supporting bio-signal measurement, the electronic device comprising:
    a pad module, at least part of the pad module is adapted to be attached to a user to obtain a bio-signal of the user, wherein the pad module includes:

a plurality of first electrodes, a first housing in which the plurality of first electrodes are disposed, and a packing member disposed on a periphery of an inside of a first sidewall included in the first housing; and a main module configured to record the bio-signal of the user transferred through the pad module, wherein the main module includes:

a plurality of second electrodes configured to make electrical contact with the plurality of first electrodes, a second housing in which the plurality of second electrodes are disposed, the second housing being coupled with the first housing in a first direction, and a plurality of magnetic bodies disposed in the second housing to correspond to positions of the plurality of second electrodes, wherein the plurality of magnetic bodies allow the plurality of first electrodes and the plurality of second electrodes to be brought into contact with each other by a magnetic force, wherein the second housing includes a protrusion disposed in a gap between the packing member and the first sidewall when the plurality of first electrodes and the plurality of second electrodes are brought into contact with each other by an attraction force of the magnetic bodies.

17. The electronic device of claim 16, wherein an available space other than a space in which the protrusion is disposed is formed in the gap.

18. The electronic device of claim 16, wherein the packing member includes:

a second sidewall configured to make contact with the inside of the first sidewall; and a third sidewall formed toward an inside of the packing member from the second sidewall and configured to form the gap between the first sidewall and the third sidewall, the third sidewall further protruding in the first direction beyond the second sidewall.

19. The electronic device of claim 18, wherein a first included angle is formed between the first sidewall and the second sidewall, the first included angle being an acute angle.

20. The electronic device of claim 18, wherein a second included angle is formed between the second sidewall and the third sidewall, the second included angle being an obtuse angle.

* * * * *